United States Patent [19]

Doyle

[11] 4,387,055

[45] Jun. 7, 1983

[54] COPPER OXALATE COMPLEXES

[75] Inventor: Gerald Doyle, Whitehouse Station, N.J.

[73] Assignee: Exxon Research and Engineering Co., Florham Park, N.J.

[21] Appl. No.: 282,651

[22] Filed: Jul. 13, 1981

[51] Int. Cl.$^3$ .............................................. C07F 1/08
[52] U.S. Cl. .......................... 260/438.1; 260/429 CY; 423/246; 585/848
[58] Field of Search ...................... 260/438.1, 429 CY; 423/246; 585/848

[56] References Cited

U.S. PATENT DOCUMENTS

| | | | |
|---|---|---|---|
| 3,809,726 | 5/1974 | Horowitz et al. | 260/438.1 X |
| 3,846,460 | 11/1974 | Fite | 260/438.1 |
| 3,923,958 | 12/1975 | Turnbo et al. | 260/438.1 X |
| 4,169,827 | 10/1979 | Gerlach et al. | 260/438.1 X |
| 4,279,874 | 7/1981 | Doyle | 423/246 |

OTHER PUBLICATIONS

Tsuda et al., J.A.C.S. 96:18, pp. 5930-5931 (1974).
A. P. Glaskova, Explosivstoffe, 23, 137-145 (1973).
W. J. Thomas et al., J. Appl. Chem. (London), 15, 17-28 (1965).

Primary Examiner—Helen M. S. Sneed
Attorney, Agent, or Firm—James H. Takemoto

[57] ABSTRACT

A cuprous oxalate complex of the formula $Cu_2(CO)_nL_mC_2O_4$ wherein L is an unsaturated hydrocarbon containing at least one non-aromatic unsaturation and n and m are numbers from 0 to 2.

9 Claims, No Drawings

COPPER OXALATE COMPLEXES

BACKGROUND OF THE INVENTION

This invention relates to copper(I) oxalate complexes. More particularly, the copper(I) oxalate complexes contain CO and/or unsaturated hydrocarbons as ligands.

U.S. Pat. No. 2,604,391 discloses a gas-producing charge for use in a non-detonating decomposition. The composition contains nitroguanidine or guanidine nitrate and a copper compound such as copper powder, cupric oxide, cuprous chloride or cuprous oxylate. A. P. Glaskova, Explosivstoffe, 23,137–145(1973) describes the effects of catalysts on the deflagration of certain classes of explosives. $Cu_2C_2O_4$ and its effects on ammonium perchlorate are shown in FIG. 8 and Table V.

It is known that certain copper(I) salts form complexes with olefins and acetylenes. For example, cuprous chloride is known to form complexes with both ethylene and acetylene. U.S. Pat. No. 3,401,112 teaches a method of separating a mixture of hydrocarbons having differing degrees of unsaturation using a copper(I) salt of the formula CuXA where XA is an anion, X is oxygen or fluorine and A is the remainder of the anion. In general, anions of the cuprous salts are anions of inorganic, organic or organo-inorganic acids, wherein the $pK_a$ values are in the order of 4.6 or less. CuXA forms a cuprous complex with said unsaturated hydrocarbon. U.S. Pat. Nos. 3,754,047 and 3,755,487 disclose a process for separating complexible ligands such as olefins, acetylenes, aromatics and CO from a feedstream using cuprous salts such as $CuAlCl_4$, $CuBF_4$, $CuOOCCF_3$, $CuPF_6$ and the like.

It is also known that certain cuprous salt solutions will absorb CO. A review of the early literature may be found in J. Appl. Chem. (London), 15, 17–28 (1965). U.S. Pat. No. 4,048,292 describes a process for recovering CO from $CO_2$-free gas streams using an absorber solution containing a copper ammonium $C_{1-2}$ acylate.

SUMMARY OF THE INVENTION

It has been discovered that cuprous oxide can react with oxalic acid and carbon monoxide to form a novel cuprous carbonyl oxalate complex wherein the carbonyl may be displaced by an unsaturated ligand. The new composition of matter comprises a cuprous oxalate complex of the formula $Cu_2(CO)_nL_mC_2O_4$ where L is an unsaturated hydrocarbon containing at least one non-aromatic unsaturation capable of forming a Cu-L bond and n and m are numbers from 0 to 2. In one preferred embodiment n is 2 and m is 0. In another preferred embodiment, n is 0 or 1 especially 0 and m is from 1 to 2.

In another aspect of the invention $Cu_2C_2O_4$ and $Cu_2(CO)_2C_2O_4$ may be prepared by a process which comprises contacting $Cu_2O$ and oxalic acid with carbon monoxide in an inert organic solvent. With regard to the preparation of $Cu_2(CO)_2C_2O_4$, $Cu_2C_2O_4$ may be isolated as an intermediate depending on the choice of solvent. Moreover, by contacting $Cu_2(CO)_2C_2O_4$ with an unsaturated hydrocarbon ligand containing at least one non-aromatic unsaturation, the CO may be partially or wholly displaced.

DETAILED DESCRIPTION OF THE INVENTION

Cupric oxalate is a well-known copper(II) complex. Cuprous oxalate complexes, however, cannot be prepared by ordinary methods, e.g., reacting $Cu_2O$ and oxalic acid in aqueous solution. The present invention relates to the discovery that if the reaction between $Cu_2O$ and oxalic is carried out in an inert organic solvent in the presence of carbon monoxide, copper(I) oxalate complexes can be isolated in high yields.

Suitable inert organic solvents are ethers, saturated hydrocarbons, aromatic hydrocarbons, esters, amines, ketones and sulfolanes. Preferred solvents are ethers and saturated aliphatic hydrocarbons substituted by halogen. Depending on the specific solvent employed, $Cu_2C_2O_4$ may be isolated as an intermediate. For example, if $Cu_2O$ is reacted with oxalic acid in the presence of CO and diethyl ether as solvent, $Cu_2C_2O_4$ is obtained in nearly quantitative yield. On prolonged contact with CO, $Cu_2C_2O_4$ is converted to $Cu_2(CO)_2C_2O_4$. On the other hand, if tetrahydrofuran is substituted for diethyl ether, $Cu_2(CO)_2C_2O_4$ is formed directly.

The reactants are combined in approximately stoichiometric amounts, i.e., about 1 mole of $Cu_2O$ per each mole of oxalic acid. CO is preferably present in excess amounts of about 1.1 to 10 moles or more per mole of $Cu_2O$. Stoichiometric amounts also may be employed. An inert atmosphere is preferred since significant amounts of oxygen may lead to oxidation of the copper(I) complex.

Reaction temperatures may range from about $-100°$ to $+100°$ C. It should be noted that at elevated temperatures, CO is released from the cuprous oxalate complex according to the reaction $Cu_2(CO)_2C_2O_4 \rightleftharpoons Cu_2C_2O_4 + 2CO$. Therefore, elevated temperatures may lead to decreased yields. Preferred temperatures are accordingly from about 0° to about 40° C.

When $Cu_2(CO)_2C_2O_4$ is contacted with unsaturated hydrocarbon L in the inert organic solvents described above, CO is displaced as illustrated by the following equilibria:

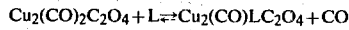

In some cases, non-stoichiometric complexes containing L may be obtained, e.g., $Cu_2$ (diphenylacetylene)$_{1.5}$-$C_2O_4$. Depending on thermodynamic considerations and reaction conditions, either a mixed complex containing CO and L or a fully displaced complex containing only L may be obtained. Preferred temperatures for the displacement reaction are from 25° to 150° C. It is also desirable to have a molar excess of L over $Cu_2(CO)_2C_2O_4$ with excesses up to 100 fold or more being preferred.

Alternatively, $Cu_2L_mC_2O_4$ where m is a number from 1 to 2 may be prepared directly by contacting $Cu_2O$, oxalic acid and unsaturated hydrocarbon L in an inert organic solvent with stirring. The red color of $Cu_2O$ gradually disappears, and $Cu_2L_mC_2O_4$ is isolated upon evaporation of solvent. This preparative technique, however, is not suitable for low molecular weight unsaturated hydrocarbons, e.g., ethylene and acetylene.

Preferred L are unsaturated hydrocarbons containing at least one ethylenic, acetylenic or isonitrilic unsaturation, more preferably $C_2$-$C_{30}$ alkene, $C_2$-$C_{30}$ alkyne, $C_8-C_{30}$ arylalkene, $C_8-C_{30}$ arylalkyne, $C_4-C_{14}$ cycloalkene or isonitrile of the formula $R-N\equiv C$ where R is $C_1-C_{20}$ alkyl, $C_3-C_{12}$ cycloalkyl, $C_7-C_{20}$ aralkyl or $C_6-C_{10}$ aryl, and most preferably $C_2-C_{20}$ alkene, $C_2-C_{20}$ alkyne, $C_8-C_{20}$ arylalkene, $C_8-C_{20}$ arylalkyne, $C_4-C_{10}$ cycloalkene or isonitrile of the formula $R-N\equiv C$ where R is $C_1-C_{10}$ alkyl, $C_6-C_{10}$ cycloalkyl, $C_7-C_{14}$ aralkyl or $C_6-C_{10}$ aryl.

$Cu_2(CO)_nL_mC_2O_4$ and methods of preparation thereof are useful in a process for separating CO and L from gas mixtures. When a gas stream containing CO is contacted with $Cu_2O$ and oxalic acid in an inert organic solvent, CO is selectively removed by forming the $Cu_2(CO)_2C_2O_4$ complex. CO may be regenerated by merely heating the solvent mixture. The resultant $Cu_2C_2O_4$ solvent mixture can then be recycled for additional reaction with CO. $Cu_2(CO)_2C_2O_4$ may also be contacted with a feedstream containing L whereby L is removed by a CO displacement reaction.

The invention is further illustrated according to the following examples:

EXAMPLE 1

A flask equipped with a dropping funnel and a gas bubbler was charged with 2.86 g of $Cu_2O$ and 75 ml of tetrahydrofuran (THF). A solution containing 1.80 g oxalic acid in 50 ml THF was added dropwise over a 30 minute period while a stream of CO was bubbled through the mixture. The red color of $Cu_2O$ changed to a whitish color over a period of 4 hours. The insoluble $Cu_2(CO)_2C_2O_4$ was isolated by filtration and characterized by elemental analysis and infrared (IR) spectroscopy.

EXAMPLE 2

The procedure of Example 1 was followed except that diethyl ether was substituted for THF. When CO was bubbled into the red $Cu_2O$ containing mixture, a color change to grey-violet was observed after several hours. A nearly quantitative yield of $Cu_2C_2O_4$ was obtained. The product was characterized by elemental analysis and IR spectroscopy. Prolonged contact of $Cu_2C_2O_4$ with CO results in conversion to $Cu_2(CO)_2C_2O_4$.

EXAMPLE 3

A mixture of 2.86 g $Cu_2O$, 14.24 g diphenylacetylene and 75 ml $CH_2Cl_2$ was stirred at room temperature while a solution of 1.80 g oxalic acid in 50 ml $CH_2Cl_2$ was added dropwise over a period of 30 minutes. The mixture was then stirred an additional four hours during which time the red color of the $Cu_2O$ gradually changed to white. The insoluble material which was isolated by filtration was analyzed and found to have the composition $Cu_2(C_6H_5C\equiv CC_6H_5)_{1.5}C_2O_4$. The complex was further characterized by infrared spectroscopy.

EXAMPLE 4

An experiment identical to that described in Example 3 was carried out except that 4.36 g cyclohexylisonitrile was substituted for the diphenylacetylene. In this case the $Cu_2O$ gradually dissolved and a clear solution was obtained. By evaporation under vacuum, a white crystalline material was isolated. This material was recrystallized from a methylene chloride-pentane mixture and identified as

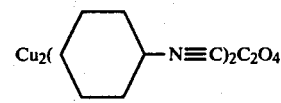

by elemental analysis and infrared and n.m.r. spectroscopy.

EXAMPLE 5

Ethylene gas was bubbled through a suspension of 2.71 g $Cu_2(CO)_2C_2O_4$ in 100 ml THF for several hours at room temperature. After this period the suspended solids were isolated by filtration. This product was identified as $Cu_2(CO)(C_2H_4)C_2O_4$.

EXAMPLE 6

A mixture of 2.71 g $Cu_2(CO)_2C_2O_4$, 2.54 grams 1-hexene and 100 ml $CH_2Cl_2$ was heated at reflux for several hours under nitrogen. After this period the suspended solids were filtered off and dried under vacuum. This complex has the composition $Cu_2(1-hexene)_{1.5}C_2O_4$.

EXAMPLE 7

A mixture of 2.71 g $Cu_2(CO)_2C_2O_4$ and 1.84 g norbornadiene in 100 ml $CH_2Cl_2$ was refluxed for four hours under nitrogen. The solid material was recovered by filtration and was characterized as

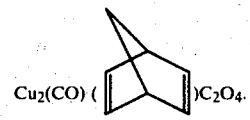

EXAMPLE 8

In the same manner as described in Example 7, 2.71 g $Cu_2(CO)_2C_2O_4$ was reacted with 1.88 g norbornylene forming

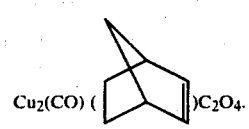

In addition, a small amount of a soluble complex with the composition

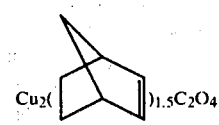

was obtained.

EXAMPLE 9

A mixture of 2.71 g $Cu_2(CO)_2C_2O_4$ and 4.32 g 1,5-cyclooctadiene (COD) in 100 ml $CH_2Cl_2$ was heated to reflux for four hours under nitrogen. The insoluble $Cu_2(CO)_2C_2O_4$ gradually went into solution. After cooling, the mixture was filtered to remove a small amount of residual solids and the clear filtrate was partially evaporated under vacuum to give a white microcrystalline precipitate. This was analyzed to be $Cu_2(COD)_{1.5}C_2O_4$.

What is claimed is:

1. A composition of matter comprising a cuprous oxalate complex of the formula $Cu_2(CO)_nL_mC_2O_4$ where L is an unsaturated hydrocarbon containing at least one non-aromatic unsaturation capable of forming a Cu-L bond and n and m are numbers from 0 to 2, provided that n and m cannot both be 0.

2. The composition of claim 1 wherein n is 0 or 1 and m is from 1 to 2.

3. The composition of claim 2 wherein L is an unsaturated hydrocarbon containing at least one ethylenic, acetylenic or isonitrilic unsaturation.

4. The composition of claim 2 wherein L is $C_2$–$C_{30}$ alkene, $C_2$–$C_{30}$ alkyne, $C_8$–$C_{20}$ arylalkene, $C_8$–$C_{30}$ arylalkyne, $C_4$–$C_{14}$ cycloalkene or isonitrile of the formula R—N≡C where R is $C_1$–$C_{20}$ alkyl, $C_3$–$C_{12}$ cycloalkyl, $C_7$–$C_{20}$ aralkyl or $C_6$–$C_{10}$ aryl.

5. The composition of claim 2 wherein L is $C_2$–$C_{20}$ alkene, $C_2$–$C_{20}$ alkyne, $C_8$–$C_{20}$ arylalkene, $C_8$–$C_{20}$ arylalkyne, $C_4$–$C_{10}$ cycloalkene or isonitrile of the formula R—N≡C where R is $C_1$–$C_{10}$ alkyl, $C_6$–$C_{10}$ cycloalkyl, $C_7$–$C_{14}$ aralkyl or $C_6$–$C_{10}$ aryl.

6. The composition of claim 2 wherein n is 0.

7. A composition of matter comprising $Cu_2(CO)_2C_2O_4$.

8. A process for preparing $Cu_2C_2O_4$ and $Cu_2(CO)_2C_2O_4$ which comprises contacting about equimolar amounts of $Cu_2O$ and oxalic acid with CO in an inert organic solvent at temperatures of from $-100°$ to $+100°$ C.

9. A process for preparing $Cu_2(CO)_nL_mC_2O_4$ where n is 0 or 1, m is from 1 to 2 and L is an unsaturated hydrocarbon containing at least one non-aromatic unsaturation which comprises contacting $Cu_2(CO)_2C_2O_4$ with at least an equimolar amount of L in an inert organic solvent at a temperature sufficient to displace CO with L.

* * * * *